US010429213B1

(12) United States Patent
Golden et al.

(10) Patent No.: US 10,429,213 B1
(45) Date of Patent: Oct. 1, 2019

(54) MONITORING INSTRUMENT AND EASILY REPLACEABLE SENSOR

(71) Applicant: United Electric Controls Co., Watertown, MA (US)

(72) Inventors: John Golden, Braintree, MA (US); Roger Iacabone, Burlington, MA (US); Levon Khatchadourian, Waltham, MA (US); Adam Karlgren, Hudson, MA (US); Andrew Liptak, Belmont, MA (US); Robert McCarey, Winthrop, MA (US); Stephen Mills, Holbrook, MA (US); John Sestito, Jr., North Attleboro, MA (US)

(73) Assignee: United Electric Controls Co., Watertown, MA (US)

( * ) Notice: Subject to any disclaimer, the term of this patent is extended or adjusted under 35 U.S.C. 154(b) by 77 days.

(21) Appl. No.: 15/599,856

(22) Filed: May 19, 2017

Related U.S. Application Data

(60) Provisional application No. 62/339,688, filed on May 20, 2016.

(51) Int. Cl.
| G01D 11/24 | (2006.01) |
| G01N 27/407 | (2006.01) |
| G01N 29/02 | (2006.01) |

(52) U.S. Cl.
CPC ....... *G01D 11/245* (2013.01); *G01N 27/4078* (2013.01); *G01N 29/02* (2013.01); *G01N 2291/021* (2013.01)

(58) Field of Classification Search
CPC .. G01D 11/245; G01D 27/4078; G01N 29/02; G01N 2291/021; G01J 5/04; G01L 19/14; G01P 1/02; G01R 1/04; G10K 11/004
USPC .................................. 73/23.42, 855, 204.22
See application file for complete search history.

(56) References Cited

U.S. PATENT DOCUMENTS

| 5,596,314 A | 1/1997 | Goldstein |
| 6,068,746 A * | 5/2000 | Kojima ................ G01N 27/407 204/421 |
| 6,322,681 B1 | 11/2001 | Weyl |
| 6,882,523 B2 | 4/2005 | Turner et al. |
| 2012/0192623 A1 | 8/2012 | Adami et al. |
| 2015/0250933 A1* | 9/2015 | Kerkhoffs .............. A61N 1/372 604/500 |

* cited by examiner

*Primary Examiner* — Natalie Huls
*Assistant Examiner* — Suman K Nath
(74) *Attorney, Agent, or Firm* — Wolf, Greenfield & Sacks, P.C.

(57) ABSTRACT

A monitoring instrument, such as a gas detection instrument, an easily replaceable sensor, and a mounting structure for the monitoring instrument. The monitoring instrument has a sensor attachment member that facilitates installation of the sensor. Alignment of the sensor during installation is facilitated by any of a number of alignment structures.

12 Claims, 6 Drawing Sheets

MONITORING INSTRUMENT AND EASILY REPLACEABLE SENSOR

CROSS-REFERENCE TO RELATED APPLICATION

The present application claims priority under 35 U.S.C. 119(e) to U.S. provisional application Ser. No. 62/339,688, titled "Monitoring Instrument with Easily Replaceable Sensor," filed May 20, 2016, which is hereby incorporated by reference in its entirety.

BACKGROUND

1. Technical Field

The techniques described herein relate generally to sensors and monitoring instruments, such as gas detection instruments, and in particular to facilitating sensor replacement.

2. Discussion of the Related Art

Gas detection instruments are used in various applications, such as in the oil and gas industry, for example. Gas detection instruments may detect the presence and/or measure concentration of gasses such as toxic gases, combustible gases, or inert gases that decrease the concentration of available oxygen. Gas detection instruments may be used for protecting health and safety of personnel or equipment and/or monitoring gases that may cause an impact to assets or the environment.

Gas detection instruments utilize sensors that may require frequent replacement. The need for frequent replacement is due at least in part to the use of gas sensor technologies which utilize consumable materials within the sensor. Depending on service conditions, sensors may need to be replaced by a technician as often as every 30 days.

SUMMARY

Some embodiments relate to a sensor. The sensor includes a housing having at least one alignment protrusion positioned to align with at least one alignment notch of a sensor attachment member of a monitoring instrument, such that the at least one alignment protrusion enters the at least one alignment notch when the sensor is installed into the sensor attachment member.

Some embodiments relate to a sensor having a beveled guide. The beveled guide is configured to align a first connector of a sensor attachment member of a monitoring instrument with a second connector of the sensor when the sensor is inserted into the sensor attachment member.

Some embodiments relate to a sensor. The sensor includes a housing having an exterior circumferential groove to engage with a toroidal spring of a sensor attachment member of a monitoring instrument.

Some embodiments relate to a monitoring instrument. The monitoring instrument includes a sensor attachment member having a housing comprising at least one alignment notch positioned such that at least one alignment protrusion of a sensor enters the at least one alignment notch when the sensor is installed into the sensor attachment member.

Some embodiments relate to a monitoring instrument. The monitoring instrument includes a sensor attachment member having a housing and a toroidal spring around an interior circumference of the housing to engage with an exterior circumferential groove of a sensor when the sensor is inserted into the sensor attachment member.

Some embodiments relate to a monitoring instrument including a sensor attachment member. The sensor attachment member has at least one compression spring, a substrate supported by the at least one compression spring, the at least one compression spring accommodating movement of the substrate, and a first connector mounted on the substrate. The first connector is configured to engage with a second connector of a sensor when the sensor is inserted into the sensor attachment member.

Some embodiments relate to a mounting structure for a monitoring instrument. The mounting structure includes a first plate having a first hook and a first hole and a second plate having a second hook and a second hole. The first and second hooks are positioned to hook onto a horizontal support member. The first and second holes are configured to receive a mounting pin.

Some embodiments relate to a method of installing a sensor at a monitoring instrument. The sensor may be pushed into a sensor attachment member of the monitoring instrument after aligning one or more alignment protrusions of the sensor with one or more alignment notches of the sensor attachment member.

The foregoing summary is provided by way of illustration and is not intended to be limiting.

BRIEF DESCRIPTION OF THE DRAWINGS

In the drawings, each identical or nearly identical component that is illustrated in various figures is represented by a like reference character. For purposes of clarity, not every component may be labeled in every drawing. The drawings are not necessarily drawn to scale, with emphasis instead being placed on illustrating various aspects of the techniques and devices described herein.

DETAILED DESCRIPTION

The inventors have recognized and appreciated various challenges that may arise with sensor replacement for monitoring instruments, such as gas detection instruments. The conditions in which sensor replacement is performed may be non-ideal for a number of reasons. Monitoring instruments may be located high off the ground, and may be accessed by a technician on a catwalk or ladder. Alternatively, monitoring instruments may be located low to the ground, and the instrument may be difficult to reach. Visibility may be limited or non-existent due to the angle at which the technician is positioned, or the environment in which the instrument located. A technician may need to install the replacement sensor while wearing gloves, which may limit the technician's manual dexterity. In some cases, monitoring instruments may be positioned outdoors and subject to inclement weather that may limit visibility. Since gas sensors may be used in an application where they are important for health, safety or other reasons, delaying installation of the replacement sensor may not be an option.

Accordingly, the need has been appreciated for a monitoring instrument, such as a gas detection instrument, which has a sensor that is easily replaceable in situ. The instrument and sensor may also need to be robust, and have robust physical and/or electrical connections so they are suitable for use in industrial environments. The present application describes such a monitoring instrument and sensor.

Figure 1:
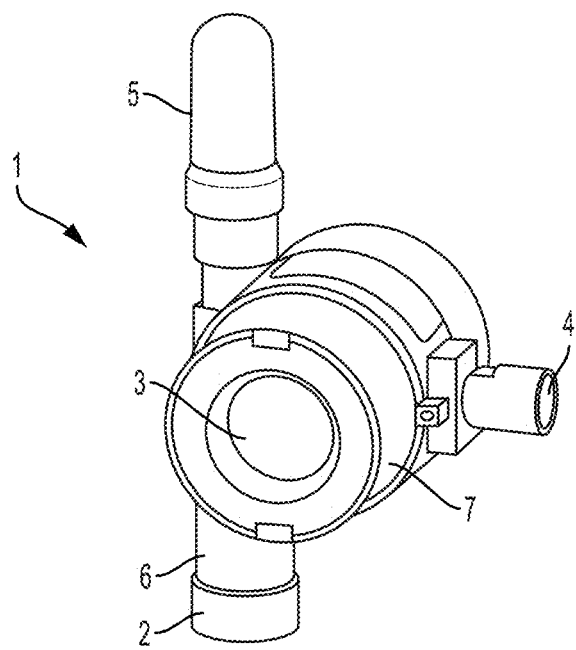
FIG. 1 shows an example of a monitoring instrument having an easily replaceable sensor, according to some embodiments.

FIG. 1 shows an example of a monitoring instrument having an easily replaceable sensor, according to some embodiments. Specifically, FIG. 1 shows a gas detection instrument 1 having a replaceable sensor 2 attached to the instrument 1 at a sensor attachment member 6. Sensor 2 may be configured to detect the presence and or concentration of one or more gases. The instrument 1 may have an explosion-proof enclosure 7. The instrument may have a display 3 that shows monitoring and or detection results (e.g., alerts or gas concentration values). The instrument 1 may have a push-button 4 that allows a user to operate the instrument 1. The instrument 1 may be battery-powered, and may house a battery within the housing of the instrument 1. The instrument 1 may have an antenna 5 that facilitates wireless communications with a host device using a suitable wireless communication protocol (e.g., the HART protocol) for providing monitoring data to the host device. The sensor 2 may use any of a variety of gas sensor technologies capable of detecting any of a variety of gases, such as hydrogen sulfide or methane, by way of example. However, the present application is not limited as to the gas sensor technology utilized or the type of gas that is detected. Also, the present application is not limited to gas sensors, as the techniques and structures described herein may be used for other types of sensors and monitoring instruments.

Figure 2:
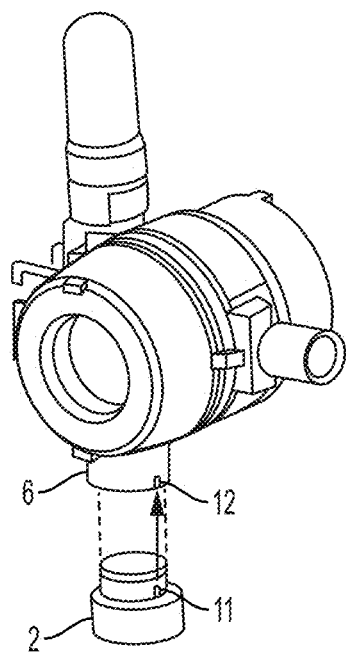
FIG. 2 illustrates installation of the replacement sensor, according to some embodiments.

FIG. 2 illustrates installation of the replacement sensor 2. Installation may be performed by aligning alignment protrusions (e.g., alignment pins 11) of the replacement sensor 2 with alignment notches 12 in the sensor attachment member 6. The sensor 2 is then pushed into the sensor attachment member 6 by applying force to the sensor 2 in the upward direction of FIG. 2. As force is applied, the alignment pins 11 enter the alignment notches 12, allowing the sensor 2 to be pushed into the sensor attachment member 6. A suitable applied force attaches the sensor 2 to the sensor attachment member 6. In some embodiments, the alignment pins 11 may be keyed exterior pins. In some embodiments (not shown), the position of the alignment pin(s) 11 and alignment notche(s) 12 may be reversed, such that the sensor 2 has alignment notches and the sensor attachment member 6 has alignment pins.

Figure 3A:
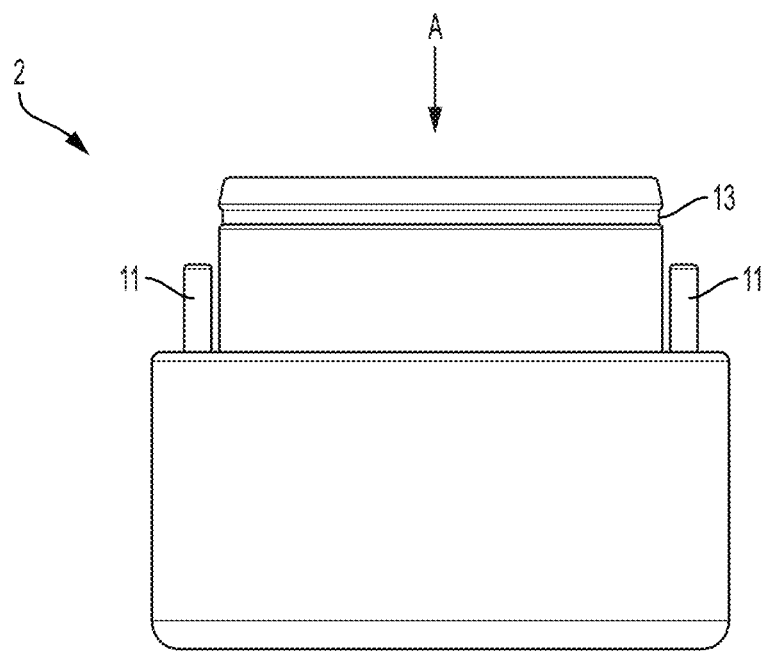
FIG. 3A shows a side view of the exterior of the sensor, according to some embodiments.
Figure 3B:
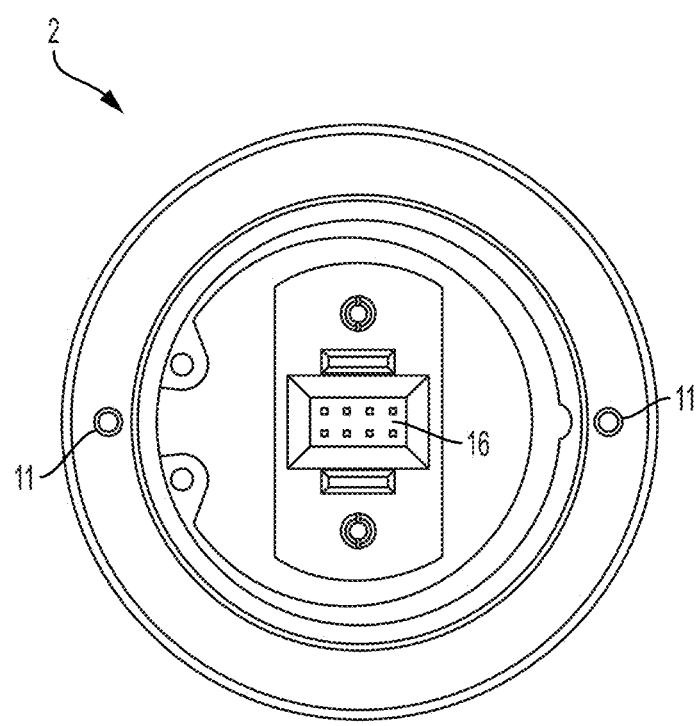
FIG. 3B shows a top view of the sensor from direction A shown in FIG. 3A.

FIG. 3A shows a side-view of the exterior of the sensor 2 in an embodiment in which the sensor 2 has alignment pins 11. The sensor 2 includes two alignment pins 11 that are positioned to align with alignment notches 12 in the sensor attachment member 6. FIG. 3B shows a top view of the sensor 2 from direction A shown in FIG. 3A. FIG. 3B shows the alignment pins 11 are positioned 180 degrees apart on the sensor 2 in the circular geometry of the sensor 2, as viewed from above. However, the techniques and devices described herein are not limited as to a circular geometry for the sensor, or the locations of the alignment pin(s) 11. The alignment pin(s) 11 may be positioned in any suitable location corresponding to the position of the alignment notche(s) 12 of the sensor attachment member 6. Any number of alignment pins 11 may be used, such as one, two, three, four or more. The alignment notches 12 of the sensor attachment member may have the same number of alignment notches as the number of pins 11, however, it is possible that the number of alignment notches 12 may be greater than the number of pins 11. The pins 11 may have a circular cross section or a cross-section having another shape such as a polygonal shape (e.g., a square, a rectangle, a hexagon, etc.). The sensor housing and alignment pins 11 may be formed of a metal (e.g., stainless steel) or another material having suitable strength and rigidity. A sensing device (not shown) capable of sensing the presence of gas and/or gas concentrations may be housed within the sensor 2. The sensing device of the sensor 2 may be electrically connected to the instrument 1 via connector 16, as discussed further below.

Figure 3C:
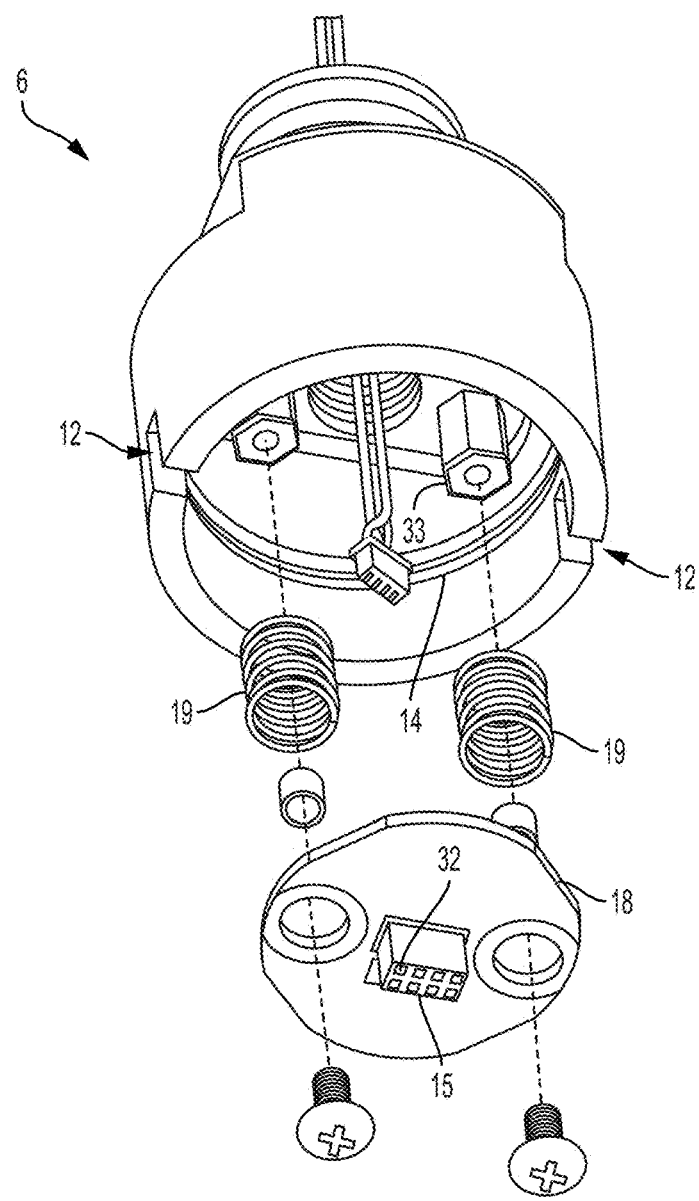
FIG. 3C shows an exploded view of the sensor attachment member, according to some embodiments.

FIG. 3C shows an exploded view of the sensor attachment member 6. Sensor attachment member 6 has a circular exterior housing with alignment notches 12 positioned to align with the alignment pins 11 of the sensor 2. As shown in FIG. 3C, the alignment notches 12 may be vertical alignment notches extending in the direction of sensor attachment. The alignment notches 12 may have any shape, so long as they are suitable for accepting the alignment pins 11. The housing of the sensor attachment member 6 may be formed of a metal (e.g., stainless steel) or another material having suitable strength and rigidity.

The alignment pins 11 and alignment notches 12 may allow coarse alignment of the sensor 2 with the sensor attachment member 6 even in conditions of low or zero visibility. The alignment pins 11 on the sensor 2 provide a coarse orientation to allow connectors on the sensor 2 and the sensor attachment member 6 to engage. In some embodiments, the alignment pins 11 allow a coarse alignment of the sensor 2 by feel. The sensor can be installed easily in blind or low ambient lighting situations simply using feel by turning the sensor until the alignment pins 11 engage with the alignment notches 12.

Additional features may provide more precise alignment for electrical connections between the sensor 2 and sensor attachment member 6. As shown in FIG. 3C, the sensor attachment member 6 may house an electrical connector 15 electrically connected (e.g., by wires) to electronics of the instrument 1. The connector 15 may have sockets 32 to accommodate pins 31 from the sensor. Eight sockets 32 are shown merely by way of illustration, as the techniques described herein are not limited to the number of pins or sockets used. FIG. 3B shows the sensor 2 has a connector 16. Connector 16 may have a plurality of pins (e.g., 8 pins) to engage with the sockets 32 of the electrical connector 15 of the sensor attachment member 6. In other embodiments, different types of electrical connectors may be used. For example, in some other embodiments (not shown), connector 15 may have pins and connector 16 may have sockets to accept the pins from connector 15.

Figure 3D:
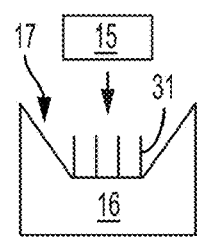
FIG. 3D shows a side view of the connectors of the sensor and sensor attachment member, according to some embodiments.

As illustrated in the embodiment shown in FIG. 3D, which shows a side view of connector 16, connector 16 may have a beveled guide 17 that aligns the connector 15 of the sensor attachment member 6 to the connector 16 of the sensor when the sensor 2 is pushed into the sensor attachment member 6. The beveled guide 17 can provide fine alignment of the electrical connectors. Beveled guide 17 is designed to engage following the coarse alignment (with the alignment pins) to provide a robust alignment of the electrical connectors as the sensor 2 is installed. Proper and robust alignment of the electrical connectors during installation prevents damage to the connectors.

As shown in FIG. 3D, the beveled guide 17 is angled such that if there is misalignment of connector 15 with connector 16, connector 15 makes contact with the angled surface of the beveled guide 17, which pushes connector 15 into alignment. Thus, as the sensor 2 is inserted (pushed) into the sensor attachment member 6, the connectors 15 and 16 engage with one another. In this example, the pins 31 of connector 16 are inserted into the sockets 32 of connector 15, thereby establishing an electrical connection between electronics of the sensor 2 and the instrument 1. In some embodiments, the beveled guide 17 may be beveled in both the vertical and horizontal dimensions, as illustrated in FIG. 3B, to provide for alignment in both the vertical and horizontal dimensions. Accordingly, the cross section of FIG. 3D of the beveled guide is applicable to both the horizontal and vertical dimensions of FIG. 3B (though two pins instead of four would be present in the cross section for the horizontal dimension). The connector 16 may be a polymeric type connector with a pin terminal array, in some embodiments.

In some embodiments, the connector 15 of the sensor attachment member 6 may be mounted on a "floating" substrate 18, such as a circuit board (e.g., a PCB) to accommodate movement of connector 15 for alignment with connector 16. Movement of substrate 18 may be accommodated by mounting it on one or more springs 19, which may be compression springs, for example. Springs 19 may be installed on one or more standoffs or pylons 33 within sensor attachment member 6. Accordingly, as the connector 15 makes contact with the beveled guide 17, the springs 19 flex to allow the substrate and connector 15 to move into a position aligned with the connector 16. The floating substrate 18 can accommodate positional variation in all three axes and/or rotation to correct angular misalignment.

The springs 19 also allow for correct installation of the sensor 2 regardless of tolerance stackups in the z-direction. This ensures that the toroidal spring 14 can properly engage each time. Engagement of the toroidal spring 14 is discussed further below.

In addition, the springs 19 supporting the "floating" printed circuit board or other substrate in the z-direction ensures that forcing the sensor 2 into place during the unlikely occurrence of misalignment will not result in permanent damage to the connector 15 on the sensor attachment member 6.

Figure 4A:
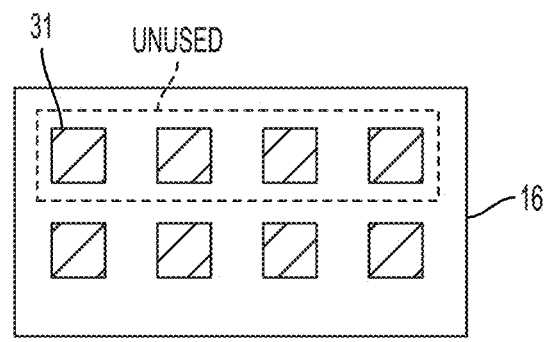
FIG. 4A shows a pin configuration of the connector of the sensor, according to some embodiments.
Figure 4B:
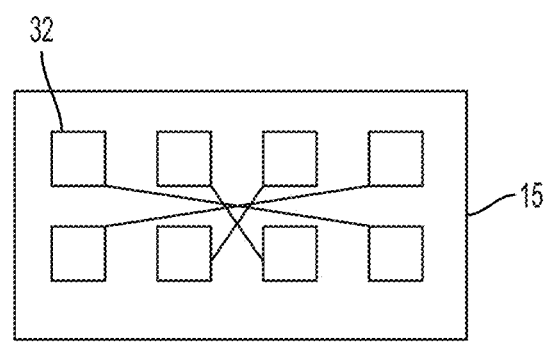
FIG. 4B shows a socket configuration of the connector of the sensor attachment member and their electrical connections, according to some embodiments.
Figure 4C:
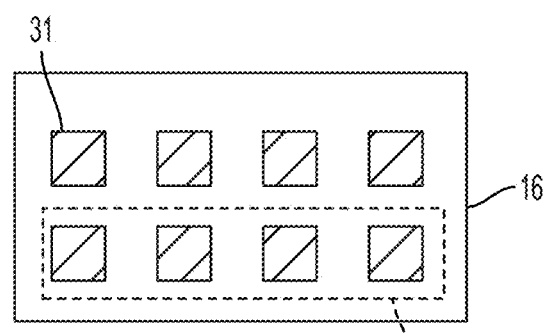
FIG. 4C shows the connector of the sensor rotated by 180 degrees, according to some embodiments.

In some embodiments, the keyed alignment pins 11 and the alignment notches 12 are symmetric, which allows the sensor 2 to engage with the sensor attachment member 6 either in the orientation shown in FIG. 2 or an orientation in which the sensor is rotated by 180 degrees. In some embodiments, the instrument 1 and sensor 2 may be designed to operate the same regardless of the angle (0 degrees or 180 degrees) at which the sensor 2 is installed in the sensor attachment member 6. The electrical connections may be designed to provide this capability. In some embodiments, only a subset of the electrical connections of the connector 16 may be used. In other words, the electronics of the sensor 2 may only transmit or receive signals through a subset of the electrical connections of the connector 16. For example, as shown in FIG. 4A, one row of four pins may not be utilized on connector 16, and the other row may have one or more pins that are utilized. At the connector 16, the pins that are in use will either be connected to the top row of sockets or the bottom row of sockets, depending on the angle (0 degrees or 180 degrees) at which the sensor 2 is installed in the sensor attachment member 6. To accommodate either orientation, the electrical connections of the sockets of connector 15 may be connected together as shown in FIG. 4B, such that regardless of whether the connector 16 is connected in the orientation shown in FIG. 4A, or an orientation rotated by 180 degrees, as shown in FIG. 4C, the instrument 1 receives the same signals from the sensor 2. As shown in FIG. 4B, each corner socket may be electrically connected to the corner socket in the opposite corner, and the interior sockets may be connected to the socket that is one over and one up (or down). As seen in FIG. 4B, the connections between the sockets are symmetric about the horizontal and vertical dimensions of FIG. 4B, which accommodates a rotation of connector 16 by 180 degrees. Accordingly, the sockets 15 receive the same electrical signal(s) regardless of the orientation in which the sensor 2 is inserted.

Upon pushing the sensor 2 into the sensor attachment member 6, a robust mechanical connection is made as follows. As shown in FIG. 3A, the sensor 2 has a groove 13 around the exterior circumference of the sensor 2. The groove 13 may extend around the entire circumference of the sensor 2, in some embodiments. As shown in FIG. 3C, the sensor attachment member 6 has a toroidal spring 14 around the interior circumference of the housing of the sensor attachment member 6. The toroidal spring 14 may extend around the entire interior circumference of the housing of the sensor attachment member 6, in some embodiments. The toroidal spring 14 protrudes from the interior of the housing of the sensor attachment member 6 into the interior of the sensor attachment member 6. Any suitable toroidal spring may be used, such as those produced under the trade name BALSEAL. When the sensor 2 is inserted into the sensor attachment member 6, the alignment pins 11 are inserted into the alignment notches 12. When the groove 13 of the sensor 2 reaches the toroidal spring 14, the toroidal spring 14 presses into the groove 13. The sensor is held in place by the toroidal spring 14 accommodated within groove 13. This feature may allow the sensor to be removed and installed without the use of hand tools. Removal of the sensor 2 may be performed simply by pulling the sensor 2 (in the downward direction of FIG. 2) with sufficient force (e.g., 5-30 lb, such as 10-20 lb, for example 15 lb).

Figure 5A:
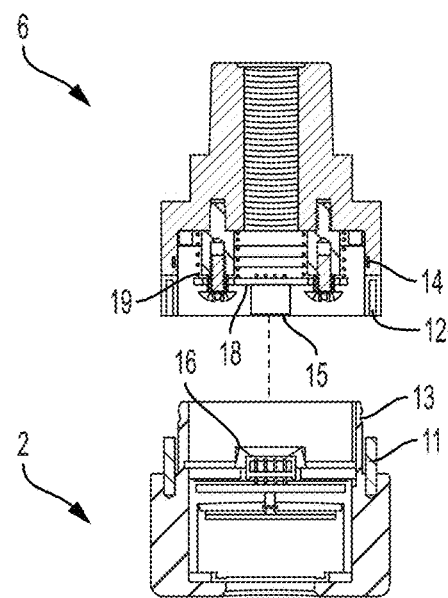
FIG. 5A shows a cross sectional view of the sensor and the sensor attachment member when separated from one another, according to some embodiments.
Figure 5B:
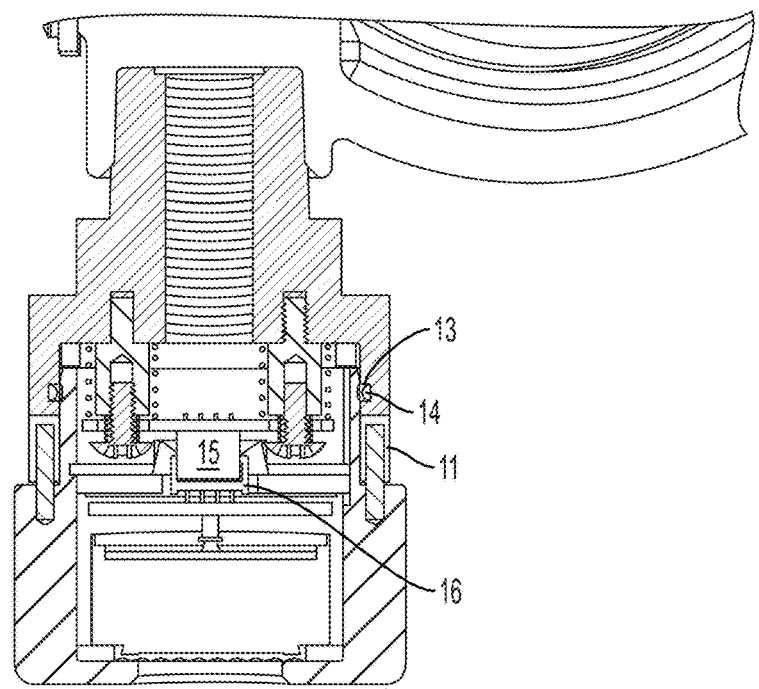
FIG. 5B shows a cross sectional view of the sensor and the sensor attachment member when attached to one another, according to some embodiments.

FIG. 5A shows a cross sectional view of the sensor 2 and the sensor attachment member 6 when separated from one another. FIG. 5B shows a cross sectional view of the sensor 2 and the sensor attachment member 6 when attached. As shown in FIG. 5B, when the sensor is attached the toroidal spring 14 of the sensor attachment member 6 sits within the groove 13, and the connectors 15 and 16 are engaged with one another.

Figure 6:
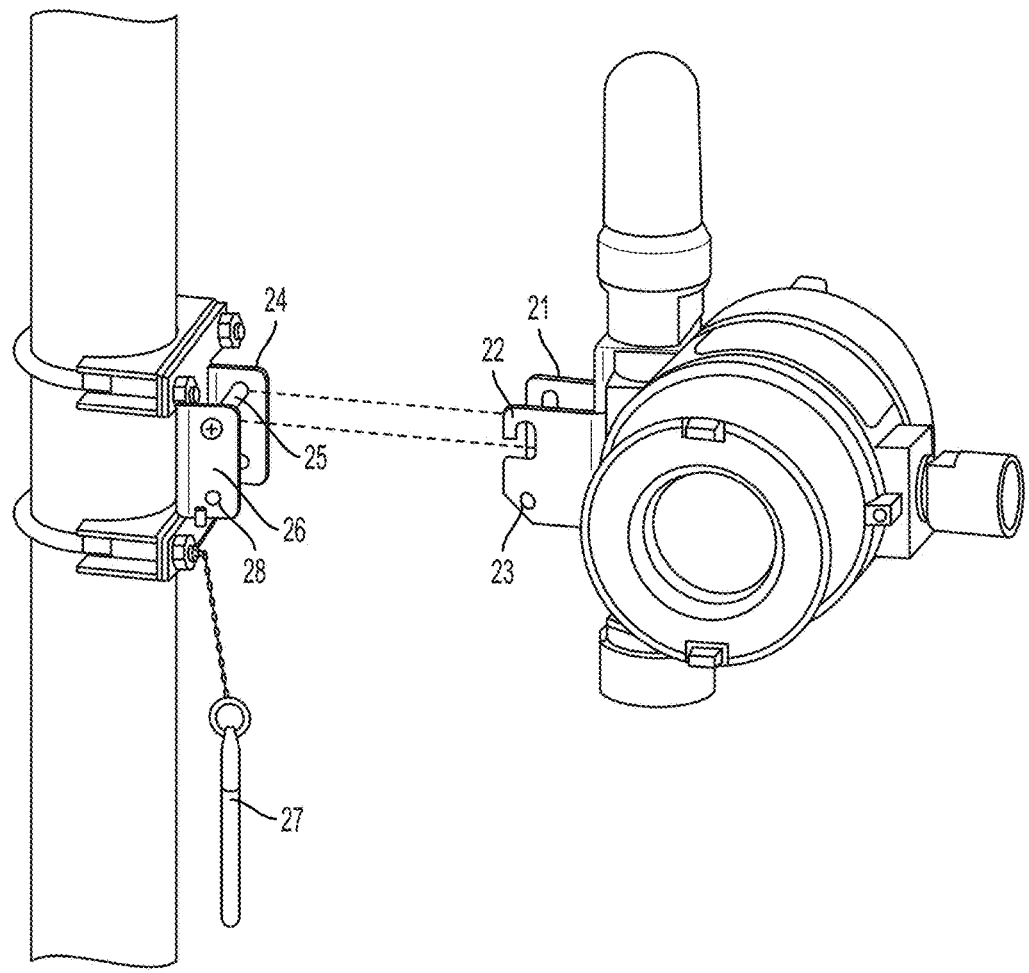
FIG. 6, FIG. 7 and FIG. 8 show a mounting apparatus for mounting the instrument, according to some embodiments.
Figure 7:
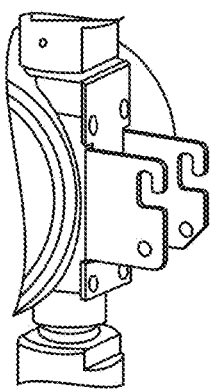
Figure 8:
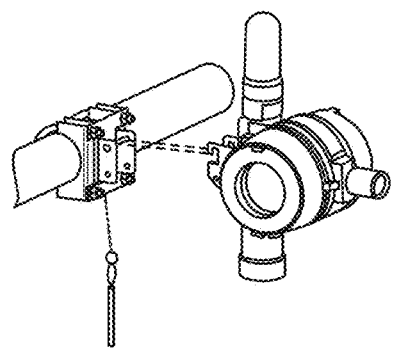

FIGS. 6-8 show a mounting apparatus for mounting the instrument 1. As shown, the mounting apparatus may be used to mount the instrument 1 on a support, including a vertical support such as a pole or wall, for example, a horizontal support, or any other support. The mounting apparatus may allow easily repositioning the instrument 1 at a desired location. The mounting apparatus may include an instrument mounting structure 21 that is attached to the instrument housing (e.g., by bolts or screws). As shown in FIG. 6, the instrument mounting structure 21 may include a pair of rigid plates formed of metal or another suitable material. Each plate may have a hook 22 and a hole 23. The mounting apparatus also includes a support structure 24 that can be attached to the support (e.g., a pole, as shown). The support structure 24 may have a horizontal support member 25 such as a pin, a rod, a bolt, etc. The support structure 24 may extend between a plurality of vertical plates 26, and may be installed in holes of the vertical plates 26. FIG. 7 shows another view of the instrument mounting structure 21. FIG. 8 shows that the support structure 24 can be attached to a horizontal support, such as a pole, a pipe, etc. During mounting of the instrument, the hooks 22 are designed to hook onto the horizontal support member 25. Then, the mounting pin 27 can be inserted into the holes 28 of the vertical plates 26.

Various aspects of the apparatus and techniques described herein may be used alone, in combination, or in a variety of arrangements not specifically discussed in the embodiments described in the foregoing description and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A sensor comprising:
    a housing;
    at least one alignment protrusion positioned to align with at least one alignment notch extending into a lower edge of an exterior housing of a sensor attachment member of a monitoring instrument, the lower edge of the exterior housing having a circular shape, such that the at least one alignment protrusion enters the at least one alignment notch when the sensor is installed into the sensor attachment member through the lower edge of the exterior housing of the sensor attachment member, wherein a portion of the housing is accommodated within the exterior housing of the sensor attachment member when the sensor is installed in the sensor attachment member; and
    a beveled guide configured to align a first connector of the sensor attachment member with a second connector of the sensor when the sensor is inserted into the sensor attachment member,
    wherein the portion of the housing has a circumferential groove to engage with a toroidal spring of the sensor attachment member.

2. The sensor of claim 1, wherein the sensor is configured to detect a gas.

3. The sensor of claim 1, wherein the at least one alignment protrusion is at least one alignment pin.

4. The sensor of claim 1, wherein the at least one alignment protrusion comprises a plurality of alignment protrusions and the at least one alignment notch comprises a plurality of alignment notches.

5. The sensor of claim 4, wherein the sensor is operable with the monitoring instrument when the sensor is installed into the sensor attachment member in a first angular orientation and a second angular orientation in which the sensor is rotated 180 degrees with respect to the first angular orientation.

6. The sensor of claim 1, wherein the circumferential groove is at an exterior of the portion of the housing.

7. A monitoring instrument, comprising:
    a sensor attachment member having:
    an exterior housing adapted to accommodate a portion of a housing of a sensor therein when the sensor is installed into the sensor attachment member through a lower edge of the exterior housing, the lower edge of the exterior housing having a circular shape; and
    at least one alignment notch extending into the lower edge of the exterior housing, the at least one alignment notch being positioned such that at least one alignment protrusion of a sensor enters the at least one alignment notch when the sensor is installed into the sensor attachment member; and
    a first connector configured to be aligned with a second connector of the sensor by a beveled guide of the sensor when the sensor is inserted into the sensor attachment member,
    wherein the portion of the housing has a circumferential groove to engage with a toroidal spring of the sensor attachment member.

8. The monitoring instrument of claim 7, wherein the at least one alignment protrusion comprises a plurality of alignment protrusions and the at least one alignment notch comprises a plurality of alignment notches.

9. The monitoring instrument of claim 8, wherein the sensor is operable with the monitoring instrument when the sensor is installed into the sensor attachment member in a first angular orientation and a second angular orientation in which the sensor is rotated 180 degrees with respect to the first angular orientation.

10. The monitoring instrument of claim 7, further comprising the toroidal spring around an interior circumference of the exterior housing to engage with the circumferential groove when the sensor is inserted into the sensor attachment member.

11. The monitoring instrument of claim 10, wherein the sensor attachment member includes:
    at least one compression spring;
    a substrate supported by the at least one compression spring, the at least one compression spring accommodating movement of the substrate, wherein the first connector is mounted on the substrate.

12. The monitoring instrument of claim 7, wherein the sensor attachment member includes:
    at least one compression spring;
    a substrate supported by the at least one compression spring, the at least one compression spring accommodating movement of the substrate, wherein the first connector is mounted on the substrate.

* * * * *